(12) United States Patent
Liu et al.

(10) Patent No.: US 11,679,072 B2
(45) Date of Patent: Jun. 20, 2023

(54) WATER-BASED SMUDGE-RESISTANT MAKE-UP REMOVER

(71) Applicant: L'OREAL, Paris (FR)

(72) Inventors: Tianyi Liu, Springfield, PA (US); Koji Endo, Kawasaki (JP)

(73) Assignee: L'OREAL, Paris (FR)

( * ) Notice: Subject to any disclaimer, the term of this patent is extended or adjusted under 35 U.S.C. 154(b) by 173 days.

(21) Appl. No.: 17/006,037

(22) Filed: Aug. 28, 2020

(65) Prior Publication Data
US 2022/0062150 A1 Mar. 3, 2022

(51) Int. Cl.
*A61Q 1/14* (2006.01)
*A61K 8/73* (2006.01)
(Continued)

(52) U.S. Cl.
CPC ............ *A61K 8/732* (2013.01); *A61K 8/0291* (2013.01); *A61K 8/25* (2013.01); *A61K 8/34* (2013.01);
(Continued)

(58) Field of Classification Search
CPC . A61Q 1/14; A61Q 1/10; A61K 8/345; A61K 8/347; A61K 8/736; A61K 8/732;
(Continued)

(56) References Cited

U.S. PATENT DOCUMENTS 5,380,455 A * 1/1995 Tsuda .................... A61Q 19/10
510/432
6,162,451 A 12/2000 Vanstraceele et al.
(Continued)

FOREIGN PATENT DOCUMENTS

FR 3 070 863 A1 3/2019
FR 3 075 049 A1 6/2019
(Continued)

OTHER PUBLICATIONS

PCT Notification of Transmittal of the International Search Report and the Written Opinion of the International Searching Authority, or the Declaration issued to counterpart Application No. PCT/US2021/047989 dated Oct. 19, 2021.
(Continued)

*Primary Examiner* — Eisa B Elhilo
(74) *Attorney, Agent, or Firm* — McNees Wallace & Nurick LLC

(57) ABSTRACT

A cosmetic composition for make-up removal that provides aesthetically pleasing gliding application and is smudge resistant, the composition being provided in the form of a water-based micellar make-up removal composition that includes a blend of surfactants that includes one surfactant that has an HLB that is in the range from about 8 to about 16 and at least one surfactant that has an HLB that is greater than 16, and one or more powdered polysaccharides provided as essentially water-insoluble particles. In some embodiments the surfactant with an HLB greater than 16 is amphoteric. The composition can also include one or more of each or a combination of inorganic mineral powders, humectants, silicone-based defoaming agents, preservatives, and other cosmetically acceptable additives.

20 Claims, 6 Drawing Sheets

(51) Int. Cl.
   *A61K 8/44* (2006.01)
   *A61K 8/02* (2006.01)
   *A61K 8/36* (2006.01)
   *A61K 8/891* (2006.01)
   *A61K 8/25* (2006.01)
   *A61K 8/41* (2006.01)
   *A61K 8/34* (2006.01)

(52) U.S. Cl.
   CPC ............. *A61K 8/345* (2013.01); *A61K 8/347* (2013.01); *A61K 8/36* (2013.01); *A61K 8/416* (2013.01); *A61K 8/442* (2013.01); *A61K 8/891* (2013.01); *A61Q 1/14* (2013.01); *A61K 2800/30* (2013.01)

(58) Field of Classification Search
   CPC .......... A61K 8/0291; A61K 8/25; A61K 8/34; A61K 8/36; A61K 8/416; A61K 8/442; A61K 8/891; A61K 2800/30
   USPC ........................................................ 510/136
   See application file for complete search history.

(56) References Cited

U.S. PATENT DOCUMENTS 7,601,680 B2 * 10/2009 Wang .................... C09K 23/54
                                                       510/136
2006/0217283 A1 * 9/2006 De Salvert ............... C11D 1/94
                                                       510/417
2008/0234159 A1 * 9/2008 Anantaneni .............. A61Q 5/02
                                                       510/420
2008/0312341 A1 * 12/2008 Futterer ................... A61Q 5/02
                                                       510/136

FOREIGN PATENT DOCUMENTS

GB         2568149 A  *  5/2019 ............. A61Q 19/10
WO      2020023185 A1     1/2020

OTHER PUBLICATIONS

Mintel, "Micellar Foaming Gel Cleanser", XP55827199, Database Record ID No. 7578871, published Apr. 2020, www.gnpd.com.
Mintel, "Safe & Mild Makeup Remover", XP55827189, Database Record ID No. 7947557, published Jul. 2020, www.gnpd.com.
Mintel, "Micellar Liquid", XP55827413, Database Record ID No. 6915473, published Oct. 2019, www.gnpd.com.
Mintel, "Micellar Liquid", XP55728044, Database Record ID No. 4595215, published Feb. 2017, www.gnpd.com.
Search Report issued for counterpart application No. FR 2011325 dated Jul. 26, 2021.

* cited by examiner

WATER-BASED SMUDGE-RESISTANT MAKE-UP REMOVER

FIELD

This invention relates to make-up removal and cleansing compositions provided in a water-based micellar system that resists smudging.

BACKGROUND

Typically, make-up removal products and cleansers are used on the entire face, including some which are necessarily used around the eyes. Indeed, there are cosmetic cleansers designed specifically for removal of stubborn make-up such as regular or waterproof mascara, eye liner, eye shadow, glitters, and long-wear foundation, in addition to longer-lasting lip products. Such cleansers can require repeated tugging and rubbing on the skin, in particular on and around delicate eye tissues, which can be inherently irritating to the skin. In addition, these make-up removing products cause smudging of the make-up rather than complete removal, requiring use of additional remover and/or other cleansers to provide a satisfactory degree of cleaning.

Accordingly, there is a need for cosmetic cleansing compositions, in particular make-up removing cleansers, with a smooth glide application to minimize tugging and prevent skin irritation and enable make-up removal with minimal smudging.

SUMMARY

The disclosure provides, in various embodiments, a cosmetic composition for make-up removal, comprising:
  i. a water-based micellar cleansing system that comprises:
    a. a blend of at least two surfactants, the blend comprising at least one nonionic surfactant having an HLB that is in the range from about 8 to about 16, and at least one surfactant having an HLB that is greater than about 16;
    b. at least one powdered polysaccharide; and
    c. water.

In accordance with some embodiments of the water-based micellar cleansing system, the at least one surfactant having an HLB that is greater than about 16 and is essentially free from (as defined herein) or excludes cationic surfactants.

In accordance with some embodiments of the water-based micellar cleansing system the at least one surfactant having an HLB that is in the range from about 8 to about 16 is a nonionic surfactant, and the at least one surfactant having an HLB that is greater than about 16 is one of an anionic and an amphoteric surfactant.

In accordance with some embodiments of the water-based micellar cleansing system, the at least one surfactant having an HLB that is greater than about 16 is an amphoteric surfactant and has an HLB that is greater than 20.

In accordance with some embodiments of the water-based micellar cleansing system, the amphoteric surfactant comprises an alkyl amphoacetate.

In accordance with some embodiments of the water-based micellar cleansing system, the at least one powdered polysaccharide is essentially water in-soluble.

In accordance with some embodiments of the water-based micellar cleansing system, the at least one powdered polysaccharide comprises particles that are isometric, anisometric or a combination thereof, and each of the particles has each of a length, a width and a thickness dimension that is in the range from about 2 μm to about 150 μm.

In accordance with some embodiments of the water-based micellar cleansing system, the at least one powdered polysaccharide comprises particles that are heterogenous in size.

In accordance with some embodiments of the water-based micellar cleansing system, the at least one powdered polysaccharide is selected from starches, alginates, celluloses, chitosan, chitin, and combinations thereof.

In accordance with some embodiments of the water-based micellar cleansing system, the blend of surfactants that comprises at least two surfactants includes Peg-7 Glyceryl Cocoate and Disodium Cocoamphodiacetate, and the at least one powdered polysaccharide is selected from *Oryza Sativa* (Rice) Starch, Oxidized Starch Acetate (Tapioca), and combinations thereof.

In accordance with some embodiments of the water-based micellar cleansing system, each of the surfactants is present in an amount in the range from about 0.3% to about 5%, based on the total weight of the composition.

In accordance with some embodiments of the water-based micellar cleansing system, the at least one powdered polysaccharide is present in an amount in the range from about 0.1% to about 30%, based on the total weight of the composition.

In accordance with some embodiments of the water-based micellar cleansing system, water is present in an amount in the range from about 65% to about 99%, based on the total weight of the composition.

In accordance with some embodiments, the cosmetic composition for make-up removal also comprises:
  ii. One or more additional components selected from:
    a. one or more mineral powders;
    b. one or more humectants;
    c. one or more preservatives;
    d. one or more defoaming agents;
    e. one or more cosmetically acceptable additives;
    f. and combinations thereof.

In accordance with some embodiments, the one or more additional components, when present, is present wherein one or more of the one or more mineral powders, when present, is selected from the group consisting of titanium oxide (e.g., $TiO_2$), Kaolin, silica, fumed silica, talc, mica, and combinations thereof; the one or more humectants, when present, is selected from Glycerin, Hexylene Glycol, and combinations thereof; the one or more preservatives, when present, is selected from Myrtrimonium Bromide, Phenoxyethanol, Hydroxyacetophenone and combinations thereof; and the one or more defoaming agents, when present, comprises Dimethicone (and) Polysorbate 65 (and) Simethicone.

In accordance with some embodiments, the one or more additional components, when present, is present wherein each of the one or more mineral powders, when present, comprises particles that are isometric, anisometric or a combination thereof, and each of the particles has each of a length, a width and a thickness dimension that is in the range from about 0.1 μm to about 100 μm.

In accordance with some embodiments, the one or more additional components, when present, is present wherein each of the one or more mineral powders, when present, comprises particles that are heterogenous in size.

In accordance with some embodiments, the one or more additional components, when present, is present wherein: each of the one or more mineral powders, when present, is present at a ratio of mineral powder to polysaccharide powder, by weight based on the total weight of the composition, at a ratio in the range from about 1:10 to about 2:1;

and each one of the least one humectant, when present, comprises a polyol and is present in an amount in the range from about 0.5% to about 5%, based on the total weight of the composition the at least one humectant; and each one of the one or more defoaming agent, when present, is present in an amount in the range from about 0.01% to about 1%, based on the total weight of the composition.

In various embodiments, the cosmetic composition for make-up removal may include more than one of each of the components, and may further include one or more cosmetically acceptable additives selected from fragrances; colorants; essential oils; fruit extracts, for example *Pyrus Malus* (Apple) Fruit Extract, and Aloe Barbadensis Leaf Juice Powder; citric acid, sodium chloride; neutralizing or pH-adjusting agents (e.g., triethylamine (TEA) and sodium hydroxide); and combinations thereof.

In some particular embodiments, the composition lacks, or is free or essentially free of cationic agents. In some particular embodiments, the composition lacks or is free or essentially free of parabens, formaldehyde, and formaldehyde-derived compounds, antimicrobials that comprise any one or more of caprylyl glycol, phenoxyethanol, hexyl glycerin, ethylhexylglycerin, octylglycerin, benzylglycerin, 3-heptoyl-2,2-propandiol, and 1,2-hexandiol; polyaminopropyl biguanide, also known as polyhexamethylene biguanide, or PHMB, and combinations thereof.

In some particular embodiments, the cosmetic composition for make-up removal includes:
  i. a water-based micellar cleansing system that comprises:
    a. a blend of at least two surfactants, the blend comprising at least one nonionic surfactant having an HLB that is in the range from about 8 to about 16, and at least one amphoteric surfactant; and
    b. at least one powdered polysaccharide comprising essentially water-insoluble particles that are isometric, anisometric or a combination thereof, wherein each of the particles has each of a length, a width and a thickness dimension that is in the range from about 2 μm to about 150 μm, the powdered polysaccharide selected from starches, alginates, celluloses, chitosan, chitin, and combinations thereof; and
    c. optionally, one or more of each or a combination of inorganic mineral powders, humectants, silicone-based defoaming agents, preservatives, and other cosmetically acceptable additives.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

BRIEF DESCRIPTION OF THE DRAWINGS

Features and advantages of the general inventive concepts will become apparent from the following detailed description made with reference to the accompanying drawings.

DETAILED DESCRIPTION

Figure 1:
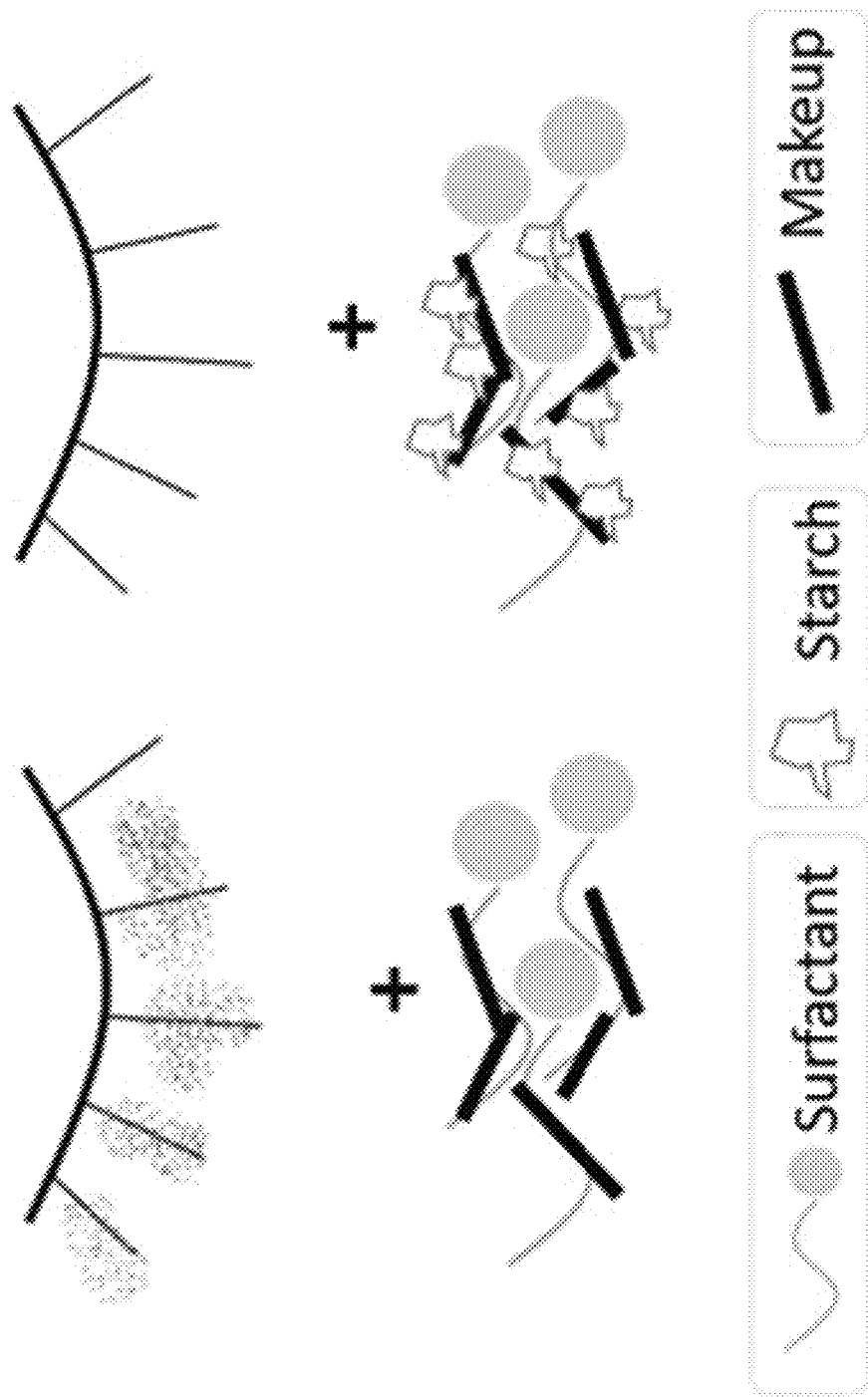
FIG. 1 is a drawing depicting a representation of a possible mechanism of make-up material capture and removal using the inventive composition.

In various embodiments, the disclosure provides a cosmetic composition for make-up removal that provides an aesthetically pleasing gliding application and is smudge resistant. In an exemplary embodiment, an inventive make-up removal composition according to the disclosure is in the form of a water-based micellar make-up removal composition comprising at least two surfactants, one or more powdered polysaccharides, and water. The composition can also include one or more inorganic mineral powders, one or more humectants, one or more silicone-based defoaming agents, one or more preservatives, and other cosmetically acceptable additives.

In various embodiments, the cosmetic composition for make-up removal may include more than one of each of the above-listed components, and may further include one or more cosmetically acceptable additives selected from fragrances; colorants; essential oils; fruit extracts, for example *Pyrus* Malus (Apple) Fruit Extract, and Aloe Barbadensis Leaf Juice Powder; citric acid, sodium chloride; neutralizing or pH-adjusting agents (e.g., triethylamine (TEA) and sodium hydroxide); and combinations thereof.

In some particular embodiments, the composition is free or essentially free of cationic agents. In some embodiments, the composition is free or essentially free of one or more of parabens, formaldehyde, and formaldehyde-derived compounds, antimicrobials that comprise any one or more of caprylyl glycol, phenoxyethanol, hexyl glycerin, ethylhexylglycerin, octylglycerin, benzylglycerin, 3-heptoyl-2,2-propandiol, and 1,2-hexandiol; polyaminopropyl biguanide, also known as polyhexamethylene biguanide, or PHMB, and combinations thereof.

"Keratinous substrate" and "keratinous tissue" each includes but is not limited to skin, hair, and nails.

"Cosmetically acceptable" means a carrier that is compatible with any keratinous substrate.

The term "micellar" as used in reference to the inventive composition means that the composition consists of a water phase with suspended micellar aggregates of surfactant and further includes suspended polysaccharide powder particles, wherein the surfactant and particles of powder are easily suspended in the water phase by agitation and which rapidly separate/phase out when the composition is at rest. The composition may be referred to as a bi-phase insofar as the dispersible particles of polysaccharide powder constitute a solid phase that is dispersible in the water based micellar water phase, though it should be understood that the composition does not include any significant oil content and thus does not include an oil phase. The composition is shaken or agitated to achieve suspension of the surfactant micelles and polysaccharide powder particles just prior to application. The pre-application agitation forms a suspension of sufficient uniformity and stability to allow a uniform application of the suspended polysaccharide particles to keratinous tissue for the removal of make-up. The composition is light-weight, much like a toner, with a pleasing feel upon application. In some embodiments, as further described herein, the composition includes one or more mineral powders in a ratio to the polysaccharide powder, by weight, of about 1:10 to 2:1 of mineral powder to polysaccharide powder.

In various embodiments, the composition is characterized through in vitro analysis, as further described in the Examples herein, as having a relatively low viscosity (i.e., less than thickened, cream type O/W, W/O and anhydrous cream cleansers). In some embodiments, as exemplified herein, the viscosity of the inventive composition is less than 1 Pa·s, and that may be in a range from about 0.0016 Pa·s to about 0.0022 Pa·s, or including from about 0.001 Pa·s to less than 1 Pa·s including all increments therebetween.

In various embodiments, the composition is characterized through in vitro analysis, as further described in the Examples herein, as having a relatively high coefficient of friction (i.e., greater than some of the comparative compositions, and in particular as compared to commercially available cream type O/W, W/O and anhydrous cream cleansers). In some embodiments, as exemplified herein, the coefficient of friction of the inventive composition is greater than 0.30μ and may be in a range from about 0.30μ to about 0.60μ or including from about 0.39μ to about 0.5μ including all increments therebetween. The greater the friction coefficient, the less greasy the composition feels on skin, conferring a fresh fell upon application that does not leave skin feeling oily and thus rendering the composition suitable as a leave-on composition that the consumer need not follow with additional cleansing.

Through the in vitro evaluations of various exemplified embodiments, the composition according to the disclosure demonstrated make-up removal performance consistent with comparative compositions with respect to glide and demonstrated a low and light viscosity and low greasiness with unexpectedly effective make-up removal performance with no or minimal smudging. As further demonstrated in the Examples, the inventors have shown that make-up removed with the inventive composition is coated with the powdered polysaccharide particles and when subjected to smudge testing, there is minimal smudging observed relative to comparative compositions that lack polysaccharide powder particles.

Without intending to be bound by theory, the inventors posit that the inventive composition provides a novel binding and capturing system whereby the suspended surfactant and starch powder particles associate with make-up and the starch powder particles bind and coat the make-up to reduce or eliminate smudging. Referring now to the drawings, FIG. 1 provides a schematic representation of the posited mechanism. The composition relies on the partial crystallinity of the polysaccharide powder particles which resist fully gelatinizing the composition and provide for a stable dispersion of the powder (after mild agitation of the composition) to permit contacting and adhering of the dispersed powder particles to the surface of make-up and concomitant adherence to the removal article (pad, tissue and the like) to deliver smudge-resistant make-up removal.

Surfactants

In accordance with the disclosure, compositions according to the disclosure includes a blend of at least two surfactants.

The term "Hydrophilic-Lipophilic Balance" or "HLB," refers to an empirical expression for the relationship of the hydrophilic and hydrophobic groups of a surfactant. This term is well known to those skilled in the art. See, e.g., "The HLB system. A time-saving guide to Emulsifier Selection" (Pub: ICI Americas Inc., 1984) and US2006/0217283 at [0053].

In some embodiments the at least two surfactants include at least one surfactant having a high Hydrophilic-Lipophilic Balance ("HLB"), and at least one surfactant having a low HLB, wherein for purposes hereof a high HLB means an HLB that is greater than 16, and wherein a low HLB means an HLB that is in the range inclusive of from about 8 to about 16.

In some embodiments, the surfactant blend includes at least two surfactants, the blend comprising at least one nonionic surfactant having an HLB that is in the range from about 8 to about 16, and at least one surfactant having an HLB that is greater than about 16, or greater than about 20.

In some embodiments, the at least one surfactant having an HLB that is greater than about 16 is essentially free from or excludes cationic surfactants.

In some embodiments the at least one surfactant having an HLB that is greater than about 16 is one of an anionic and an amphoteric surfactant.

In some embodiments, the at least one surfactant having an HLB that is greater than about 16 is an amphoteric surfactant and has an HLB that is greater than 20. In some embodiments, the amphoteric surfactant comprises an alkyl amphoacetate.

In some particular embodiments the at least two surfactants comprise each of Peg-7 Glyceryl Cocoate and Disodium Cocoamphodiacetate.

In accordance with the disclosure, suitable nonionic surfactants include Peg-7 Glyceryl Cocoate, as exemplified in the inventive compositions herein. More generally, surfactants suitable for use as a surfactant having a low HLB that is in the range inclusive of from about 8 to about 16 include nonionic surfactants, for example, but not limited to, Peg-7 Glyceryl Cocoate, Peg-30 Glyceryl Stearate, Poloxamer 124, Poloxamer 184, Polyglyceryl-6 caprylate, Polyglyceryl-4 Caprate, Caprylyl/Capryl Glucoside, Coco glucoside, and combinations thereof.

In accordance with the disclosure, suitable amphoteric surfactants include Disodium Cocoamphodiacetate, as exemplified in the inventive compositions herein. More generally, surfactants suitable for use as a surfactant having a high HLB that is greater than 16, or greater than 20 include amphoacetates, for example, but not limited to amphoteric surfactants selected from Disodium cocoamphodiacetate, sodium cocoamphoacetate, Coco-betaine, Cocamidopropyl betaine, and combinations thereof; and anionic surfactants, for example, but not limited to, Diethylhexyl sodium sulfosuccinate, disodium laureth sulfosuccinate, Sodium lauroyl sarcosinate, and combinations thereof.

The amount of each of the at least two surfactants present in the composition is provided in a range of from about 0.3% to about 5% by weight, or from about 0.5% to about 3% by weight, or from about 0.8% to about 1.5% or any suitable combination, sub-combination, range, or sub-range thereof by weight, based on the weight of the composition. One of ordinary skill in the art, however, will appreciate that other ranges are within the scope of the invention.

Thus, each of the at least two surfactants in the composition is present by weight, based on the total weight of the composition, from about 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, to about 5 percent, including increments and ranges therein and there between.

Powdered Polysaccharide

In accordance with the disclosure, compositions according to the disclosure include at least one powdered polysaccharide. In some embodiments, the at least one powdered polysaccharide is essentially water-insoluble.

Figure 2:
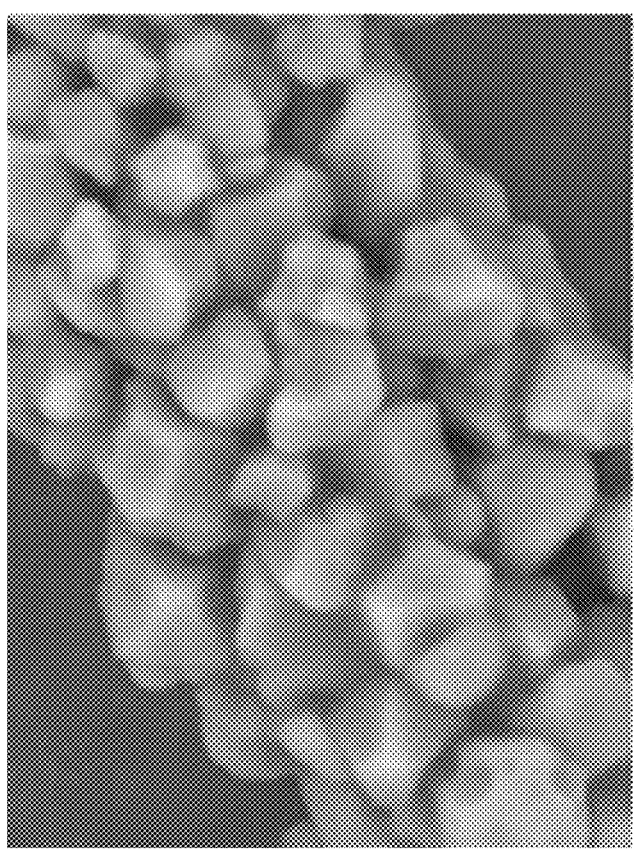
FIG. 2 is a photographic image obtained from microscopic analysis of polysaccharide powder particles on make-up the image representing an SEM image.

In the various embodiments, the at least one powdered polysaccharide comprises particles or granules that are generally irregular, or globular in shape. Referring now to FIG. 2, the depicted photograph is an SEM image that shows a plurality of powdered polysaccharide particles comprising starch at a magnification of 5000× coated essentially uniformly on a make-up substrate comprising mascara. The depicted starch particles as shown represent a plurality of particles that are heterogeneous in size and in the form of irregularly shaped granules, each having a shape that is faceted (or may be described as similar to popped pop-corn), with a plurality of irregularly spaced peaks/points and divots.

In the various embodiments, the particles may be either isometric, anisometric or a combination thereof. The particles have length, width and thickness dimensions that are in the range from about 2 µm to about 150 µm. In some embodiments, the maximum size dimension for any powdered polysaccharide particle is not greater than or is less than about 150 µm. Thus, in some embodiments, the powdered polysaccharide particles may have a mixture of sizes (i.e., they are heterogenous in size), each particle having each of length, width and thickness dimensions that may vary in the range from about 2 µm to about 150 µm. In other embodiments, the powdered polysaccharide particles may be generally homogeneous in size, wherein all of the particles are essentially the same in their overall dimensions of length, width and thickness. In these various embodiments, the particles may have overall dimensions of length, width and thickness in the range from about 2 µm to about 20 µm, or from about 25 µm to about 50 µm, or from about 50 µm to about 100 µm, or from about 100 µm to about 150 µm, or all at about 25 µm, or all at about 50 µm, or all at about 100 µm, or all at about or less than about 150 µm.

In the various embodiments, the at least one powdered polysaccharide comprises particles comprising polysaccharide that has is at least partially amorphous and partially crystalline. In some embodiments the particles are characterized as having an outer portion that is generally amorphous and an inner portion or core that is generally crystalline wherein the center has a harness that is greater than the hardness of the outer portion. In some embodiments, the outer portion is hydrated and the inner portion is free or essentially free of water.

In some embodiments the at least one powdered polysaccharide includes at least one powdered polysaccharide may be natural (i.e., plant, animal, or bacterial based), synthetic, or modified, and may be selected from one of the groups that include starches, alginates, celluloses, chitosan, chitin, and combinations thereof. In some embodiments, the at least one powdered polysaccharide includes starch, starch derivatives, cellulose (for example, but not limited to, ethylcellulose, nitrocellulose, hemicellulose, and hemicellulose derivatives), alginates, including but not limited to, sodium alginate, chitosan, chitosan derivatives, chitin, and combinations thereof.

In some particular embodiments the at least one powdered polysaccharide comprises one or more of starch and starch derivatives, wherein the starch or starch derivative is one of natural (i.e., plant or bacterial based), synthetic, or a modified starch.

In some particular embodiments the at least one powdered polysaccharide comprises plant based starch.

In some particular embodiments the at least one powdered polysaccharide comprises one of *Oryza Sativa* (Rice) Starch, starch acetate, Oxidized Starch Acetate (Tapioca), *Zea Mays* (corn) starch, and combinations thereof.

The amount of each one of the at least one powdered polysaccharide is present in the composition in a range of from about 0.1% to about 30%, or from about 0.5% to about 25%, or from about 1% to about 20%, or from about 1.5% to about 15%, or from about 2% to about 12%, or from about 2.5% to about 6%, or up to and not more than about 3%, or is at least about 3%, or from about 1% to about 3%, or from about 3% to about 10%, or from about 3% to about 15%, or from about 3% to about 30%, or any suitable combination, sub-combination, range, or sub-range thereof by weight, based on the weight of the composition. In the various embodiments, the total amount of powdered polysaccharide is not more than about 30%, and in some embodiments is not more than about 20%, and in some embodiments is not more than about 10%, and in some embodiments is not more than about 3%, wherein an excess amount of powdered polysaccharide can cause gelling of the compositions rendering unsuitable for application as a micellar water composition. One of ordinary skill in the art, however, will appreciate that other ranges are within the scope of the invention.

Thus, each one of the at least one powdered polysaccharide is present by weight, based on the total weight of the composition, from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 4.0, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29 to about 30 percent, including increments and ranges therein and there between.

Optionally, in some embodiments, the powdered polysaccharide particles are provided with additional particles selected from inorganic mineral powders selected from titanium oxide (e.g., $TiO_2$), Kaolin, silica, fumed silica, talc, mica, and the like.

In the various embodiments, inorganic mineral powders comprise particles that may be either isometric, anisometric or a combination thereof. The inorganic mineral powder particles have length, width and thickness dimensions that are in the range from about 0.1 µm to about 100 µm. In some embodiments, the maximum size dimension for any inorganic mineral powder particle is not greater than or is less than about 100 µm, and in some embodiments, is not greater than or is less than about 1 µm, or about 0.5 µm or about 0.4 µm. Thus, in some embodiments, the inorganic mineral powder particles may have a mixture of sizes (i.e., they are heterogenous in size), each particle having each of length, width and thickness dimensions that may vary in the range from about 0.1 µm to about 100 µm. In other embodiments, the inorganic mineral powder particles may be generally homogeneous in size, wherein all of the particles are essentially the same in their overall dimensions of length, width and thickness. In some specific embodiments, the inorganic mineral powders comprise which has a median particle size in the range from about 0.2 to about 0.4 µm. In these various embodiments, the inorganic mineral powder particles may have overall dimensions of length, width and thickness in the range from about 0.1 µm to about 0.5 µm, or from about 0.1 µm to about 0.4 µm, or from about 0.1 µm to about 100 µm, or from about 0.1 µm to about 75 µm, or all at about 1 µm, or all at about 0.5 µm, or all at about 50 µm, or all at about or less than about 100 µm.

The inorganic mineral powder particles are present in a ratio of mineral particle to powdered polysaccharide particles that is in a range from about 1:10 to 2:1, by weight, based on the total weight of the composition. The inventors have determined that the use of mineral particles can be beneficial in preventing agglomeration and/or clumping of precipitated powdered polysaccharide particles, thus aiding in powder dispersion when the composition is agitated prior to application.

Accordingly, the amount of inorganic mineral powder particles, when present, may be present in the composition in a range of from about one tenth of the amount of the powdered polysaccharide particles to about twice the amount of the powdered polysaccharide particles. Thus, the inorganic mineral powder particles may be present in the composition in a range of from about 0.01% to about 3%, or from about 0.1% to about 30%, or from about 0.2% to about 60%, or any suitable combination, sub-combination, range, or sub-range thereof by weight, based on the weight of the composition.

In some embodiments, the inorganic mineral powder particles may be present in the composition in a range of from about 0.01% to about 3%, or from about 0.05% to about 2.5%, or from about 0.1% to about 2.0%, or from about 0.15% to about 1.5%, or from about 0.2% to about 1.2%, or from about 0.25% to about 0.6%, or at or at least about 0.3%, or any suitable combination, sub-combination, range, or sub-range thereof by weight, based on the weight of the composition. And, in some embodiments, the inorganic mineral powder particles may be present in the composition in a range of from about 0.1% to about 30%, or from about 0.5% to about 25%, or from about 1% to about 20%, or from about 1.5% to about 15%, or from about 2% to about 12%, or from about 2.5% to about 6%, or at or at least about 3%, or any suitable combination, sub-combination, range, or sub-range thereof by weight, based on the weight of the composition. And, in some embodiments, the inorganic mineral powder particles may be present in the composition in a range of from about 0.2% to about 60%, or from about 1.0% to about 50%, or from about 2% to about 40%, or from about 3% to about 30%, or from about 4% to about 25%, or from about 5% to about 12%, or at or at least about 6%, or any suitable combination, sub-combination, range, or sub-range thereof by weight, based on the weight of the composition. One of ordinary skill in the art, however, will appreciate that other ranges are within the scope of the invention.

Thus, each one of the at least one inorganic mineral powder particles, when present, is present by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 4.0, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 percent, including increments and ranges therein and there between.

Humectant

In accordance with the disclosure, one more humectants may be present in the compositions. In some embodiments, the humectant may comprise one or more of polyols, including, for example, glycerin, glycerol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the compositions include the humectants comprising glycerin and hexylene glycol.

In accordance with the various embodiments, the amount of each humectant, when present in the composition, can range from about 0.5% to about 5% by weight, or from about 0.8% to about 3% by weight, or from about 1% to about 1.5% or any suitable combination, sub-combination, range, or sub-range thereof by weight, based on the weight of the composition. One of ordinary skill in the art, however, will appreciate that other ranges are within the scope of the invention.

Thus, each of the at least one humectant in the composition, when present, is present by weight, based on the total weight of the composition, from about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, to about 5 percent, including increments and ranges therein and there between.

Defoaming Agents/Oil

In accordance with the disclosure, one or more defoaming agents may be present in the compositions. In some embodiments, the one or more defoaming agents may comprise oil. Thus, in the various embodiments, the one or more defoaming agents, when present, may be selected from Dimethicone (and) Polysorbate 65 (and) Simethicone, dimethicone, simethicone and alcohol, and combinations thereof.

In some embodiments, the one more defoaming agent comprises Dimethicone (and) Polysorbate 65 (and) Simethicone.

In accordance with the various embodiments, the amount of each one of the one more defoaming agents present in the compositions can range from about 0.01% to about 1% by weight, or from about 0.02% to about 0.5% by weight, or from about 0.03% to about 0.1% or any suitable combination, sub-combination, range, or sub-range thereof by weight, based on the weight of the composition. One of ordinary skill in the art, however, will appreciate that other ranges are within the scope of the invention.

Thus, each one of the one more defoaming agents, when present in the composition, is present by weight, based on the total weight of the composition, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, to about 1 percent, including increments and ranges therein and there between.

Preservatives

In accordance with the disclosure, one or more preservatives may be present in the composition. In some embodiments, the one or more preservatives, when present, may be selected from Myrtrimonium bromide, phenoxyethanol, hydroxyacetophenone, ethylhexyl glycerin, chlorphenesin, cetrimonium chloride, caprylyl glycol, hexyl glycerin, octylglycerin, benzylglycerin, 3-heptoyl-2,2-propandiol, and 1,2-hexandiol; polyaminopropyl biguanide, also known as polyhexamethylene biguanide, or PHMB, and combinations thereof. In some embodiments, the composition is free or essentially free of one or more of caprylyl glycol, phenoxyethanol, hexyl glycerin, ethylhexylglycerin, octylglycerin, benzylglycerin, 3-heptoyl-2,2-propandiol, and 1,2-hexandiol; polyaminopropyl biguanide, also known as polyhexamethylene biguanide, or PHMB.

In some embodiments, the one more preservatives includes Myrtrimonium bromide, phenoxyethanol, hydroxyacetophenone, and combinations thereof.

In accordance with the various embodiments, the amount of each one of the one more preservatives present in the compositions can range from about 0.01% to about 1% by weight, or from about 0.02% to about 0.5% by weight, or from about 0.03% to about 0.1% or any suitable combination, sub-combination, range, or sub-range thereof by weight, based on the weight of the composition. One of ordinary skill in the art, however, will appreciate that other ranges are within the scope of the invention.

Thus, each one of the one more preservatives, when present in the composition, is present by weight, based on the total weight of the composition, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 percent, including increments and ranges therein and there between.

Optional Additives

The compositions can also comprise at least one additive used in the cosmetics field which does not affect the properties of the compositions according to the invention, such as additives selected from fragrances, vitamins, colorants; essential oils; fruit extracts, for example *Pyrus* Malus (Apple) Fruit Extract, and Aloe Barbadensis Leaf Juice Powder; citric acid, sodium chloride; neutralizing or pH-adjusting agents (e.g., triethylamine (TEA) and sodium hydroxide); and combinations thereof.

Although the optional active additives are given as examples, it will be appreciated that other optional components compatible with cosmetic applications known in the art may be used. Although the optional additives are given as examples, it will be appreciated that other optional components compatible with cosmetic applications known in the art may be used.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Water

In accordance with the various embodiments, water is present in the compositions in a range from about 65% to about 99%, or from about 70% to about 90%, or from about 75% to about 80%, or from about 65%, or from about 75%, or from about 85%, or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99 weight percent, including increments and ranges therein and there between The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

In some embodiment, the pH of the composition is not limited but is generally between 5 and 9, and in some embodiments, is one of between 6 and 8, and in some embodiments is 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the composition is free or essentially free of cationic agents, wherein for purposes hereof, free or essentially free means that any cationic agent is present in an amount that is at or below 0.1% by weight, based on the total weight of the composition.

EXAMPLES

Example 1: Inventive Compositions

Various representative embodiments of the inventive compositions are exemplified herein.

Exemplary embodiments of inventive compositions in the form of make-up removing compositions according to the disclosure are provided in Table 1.

TABLE 1

Inventive Compositions

| Ingredient | INV 1 | INV 2 | INV 3 |
|---|---|---|---|
| Surfactant | | | |
| Peg-7 Glyceryl Cocoate | 0.8-1.1% | 0.8-1.1% | 0.8-1.1% |
| Disodium Cocoamphodiacetate* | 0.3-0.5% | 0.3-0.5% | 0.3-0.5% |
| Powder | | | |
| Oryza Sativa (Rice) Starch | 3% | 10% | 0 |
| Oxidized Starch Acetate (Tapioca) | 0 | 0 | 3% |
| Humectant | | | |
| Polyol | 3% | 3% | 3% |
| Preservative | | | |
| Preservative Blend | ~0.6% | ~0.6% | ~0.6% |
| Defoaming Agent | | | |
| Silicone Oil | <0.05% | <0.05% | <0.05% |
| QS | | | |
| Deionized Water | QS | QS | QS |
| Evaluations | | | |
| Zero Shear Viscosity (Pa · s) | $1.98 \times 10^{-3}$ | $2.22 \times 10^{-3}$ | $1.76 \times 10^{-3}$ |
| Smudging (Latex mascara) | 1 | 1 | 1 |
| Smudging (Waterproof mascara) | 1 | 1 | 2 |
| Friction Coefficient | 0.41 | 0.5 | 0.39 |

*RM concentration in this reagent is at 30%, by weight

Inventive Compositions 1, 2 and 3 are each essentially the same composition except INV 1 includes 3% rice starch, INV 2 includes 10% rice starch, and INV 3 includes 3% tapioca starch. Each demonstrates favorable smudge resistance, as more fully described herein below, and each demonstrates viscosity and shear friction properties that are generally comparable to comparative compositions, as more fully described herein below.

Example 2: Comparative Compositions

Exemplary embodiments of inventive compositions in the form of cleansing and make-up removing compositions according to the disclosure are provided in Tables 2 & 3

TABLE 2

Comparative Compositions (with similar micellar architecture)

| Ingredient | COMP 1 | COMP 2 | COMP 3 |
|---|---|---|---|
| Surfactant | | | |
| Peg-7 Glyceryl Cocoate | 0.8-1.1% | 0.8-1.1% | |
| Disodium Cocoamphodiacetate* | 0.3-0.5% | 0.3-0.5% | 0.3-0.5% |
| Powder | | | |
| Oryza Sativa (Rice) Starch | 0 | 0 | |
| Silica | 0 | 3% | |
| Humectant | | | |
| Polyol | 3% | 3% | 3% |
| Preservative | | | |
| Preservative Blend | ~0.6% | ~0.6% | <0.1% |
| Defoaming Agent | | | |
| Silicone Oil | <0.05% | <0.05% | |
| QS | | | |
| Deionized Water | QS | QS | |
| Zero Shear Viscosity (Pa · s) | $1.60 \times 10^{-3}$ | $1.74 \times 10^{-3}$ | $1.65 \times 10^{-3}$ |
| Smudging Index (Latex mascara) | 2 | 2 | 3 |
| Smudging Index (Waterproof mascara) | 3 | 3 | 2 |
| Friction Coefficient | 0.36 | 0.37 | 0.34 |

*RM concentration in this reagent is at 30%, by weight

Comparative Compositions 1 and 2 are each essentially the same as Inventive composition INV 1, EXCEPT COMP 1 lacks any starch powder, and COMP 2 includes silica in place of starch powder. Comparative Composition COMP 3 has a micellar architecture that is similar to comparative compositions COMP 1 and COMP 2 but includes a different surfactant composition and lacks starch powder. Each of these comparative compositions demonstrates poor smudge resistance, as more fully described in the Examples herein below.

Table 3

Comparative Compositions (with different micellar architecture)

| | COMP 4 | COMP 5 |
|---|---|---|
| INGREDIENTS | Water, Cyclopentasiloxane, Isohexadecane, Sodium Chloride, Poloxamer 184, Hexylene Glycol, Dipotassium Phosphate, Benzyl Alcohol, Potassium Phosphate, Quaternium-15, Benzalkonium Chloride, Parfum/Fragrance, Citronellol, Geraniol. | Water, Peg-6 Caprylic/capric Glycerides, Cucumis Sativus (cucumber) Fruit Extract, Mannitol, Xylitol, Rhamnose, Fructooligosaccharides, Propylene Glycol, Disodium EDTA, Cetrimonium Bromide. |
| Zero Shear Viscosity (Pa · s) | $2.51 \times 10^{-3}$ | $1.57 \times 10^{-3}$ |
| Smudging Index (Latex mascara) | 3 | 3 |
| Smudging Index (Waterproof mascara) | 3 | 2 |
| Friction Coefficient | 0.21 | 0.43 |

Comparative Compositions 4 and 5 are water-based micellar compositions with a different architecture as compared to the Inventive Compositions and Comparative Compositions 1-3. Each of the Comparative Compositions COMP 3 and COMP 5 lacks starch powder. Each demonstrates poor smudge resistance, as more fully described herein below.

Example 3: Microscopic Examination of Make-Up Removal with Selected Inventive and Comparative Compositions A study was undertaken to evaluate microscopically the properties of mascara removed using selected Inventive and Comparative Compositions as included in the foregoing Examples.

Study Method: Mascara and selected compositions were provided. For each tested composition, an aliquot of ~0.1 g of Latex mascara (Commercial Benchmark) was first deposited onto glass slide and dried for 1 hour. Then ~0.5 g each of the selected Compositions was used to remove the mascara from the slide. For select Compositions, as listed in Table 4, below, a removed mascara piece was picked up for SEM imaging.

Table 4

Selected Compositions for Microscopic Evaluation

| Tested Composition | Powder Particle |
| --- | --- |
| INV 1 | Rice Starch (3%) |
| COMP 1 | None |
| COMP 2 | Silica |

Figure 3:
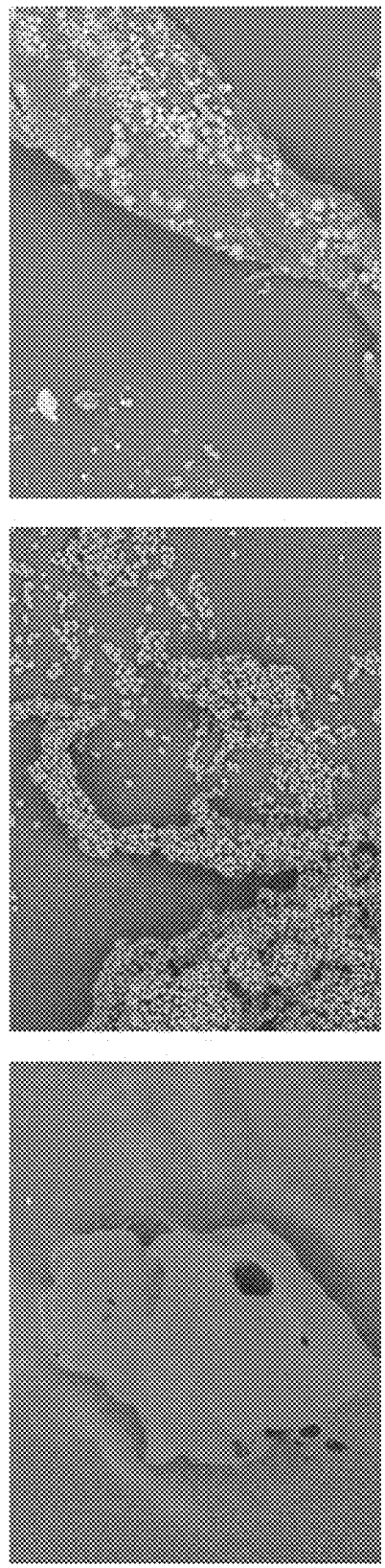
FIG. 3 includes three panels designated as A, B and C of photographic images obtained from microscopic analysis of removed make-up material representing a SEM image.

Referring now to the drawings, FIG. 3 shows a series scanning electron micrograph (SEM) images for each of compositions that include COMP 1, INV 1, and COMP 2, in that order (left (A), middle (B), right (C)). SEM image FIG. 3A is shown at 150×, and images FIG. 3B and FIG. 3C are shown at 500×.

FIG. 3A, corresponding to Comparative Composition COMP 1, shows mascara removed by this composition without any starch. The film former and wax is removed through a dissolving mechanism and the edge of removed mascara is smooth. The removed mascara pieces have no powder particle coating, this leaving the entire portion of the mascara surface open to smudging. As shown in the mascara smudging evaluation studies in the Examples below, repeated wiping of mascara treated with this comparative remover results in undesirable smudging.

FIG. 3C shows mascara removed by Comparative Composition COMP 1. Compare to starch, silica is a hard particle. The coating on the mascara by such hard particle is not complete, and further wiping may cause exposed mascara surface to be dissolved. The removed mascara pieces are only irregularly and incompletely coated with rice starch, leaving large areas of the mascara surface open to smudging. As shown in the mascara smudging evaluation studies in the Examples below, repeated wiping of mascara treated with this comparative remover results in undesirable smudging.

FIG. 3B shows mascara removed by Inventive Composition INV 1. The removed mascara pieces are completely coated with rice starch. As shown in the mascara smudging evaluation studies in the Examples below, repeated wiping of mascara treated with this inventive remover results in low smudging.

Figure 4:
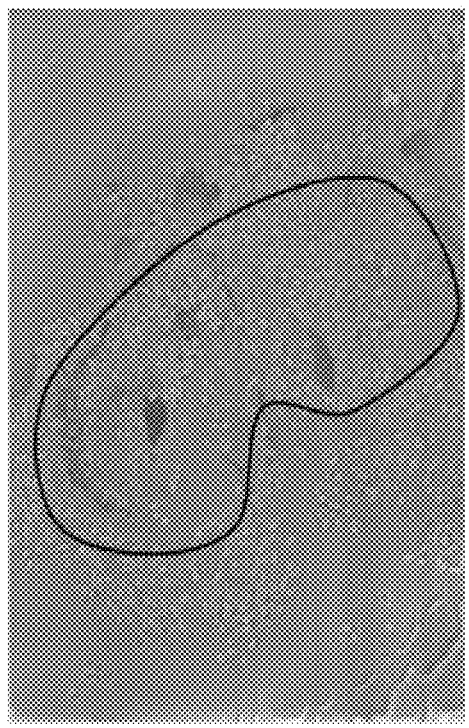
FIG. 4 includes two panels designated as A, B of photographic images obtained from microscopic analysis of removed make-up material representing a microscopic image.
Figure 4:

Referring now to FIG. 4, two images, corresponding, respectively, from left to right, to light microscopy (FIG. 4A) and SEM (FIG. 4B) images, show the mascara piece from FIG. 3B in cross section, showing in detail the extent to which the mascara piece is encased in bound starch particles, conferring resistance to smudging without compromising ease of application and glidability of the inventive composition for the removal of make-up, as further illustrated in the Examples herein below.

Example 4: Mascara Smudging Evaluation

An in-vitro study was conducted to evaluate the smudge resistance of each of a panel of selected Inventive and Comparative compositions Study Method: False eyelashes, mascara (high latex type and waterproof type) and synthetic keratinous tissue (bioskin were provided. A control study was conducted to demonstrate a standard for rating smudging/resistance to smudging. In the study, 30 strokes of mascara were applied onto fake lashes. Two types of mascaras were tested; high latex (Commercial Benchmark) and waterproof (Commercial Benchmark). After drying overnight, the fake lash is placed onto a piece of bioskin. A piece of cotton round is wetted with 1.5 g of make-up remover then attached to a mechanical probe. A preselected force of 450 g is loaded onto the probe, then wiping across the fake lashes 15 times to remove mascara.

Figure 5:
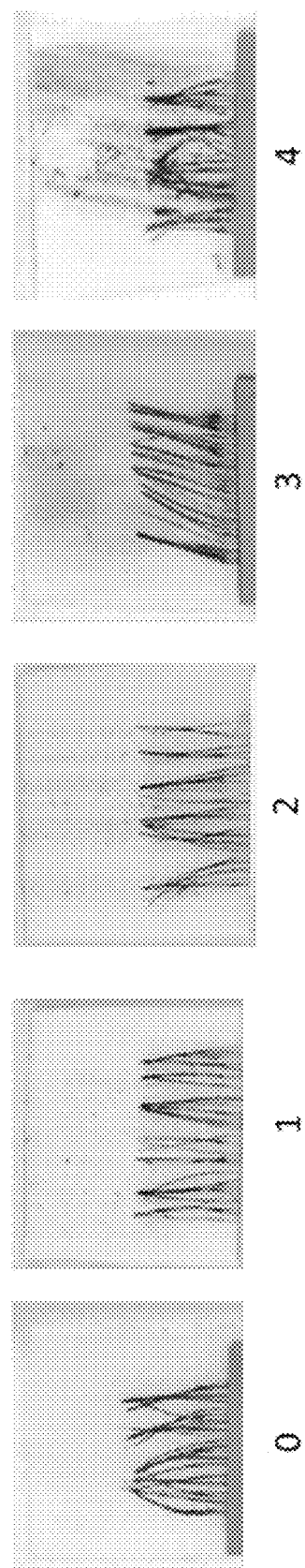
FIG. 5 is a panel of photographic images denoted as 1, 2, 3, and 4 demonstrating mascara smudging using different make-up removers on different forms of mascara.

Smudging is rated base on the below index (Smudging Index), which numbers below correspond with the numbered photographic images shown in FIG. 5:

0—No smudge at all
1—A little smudge, make-up does not leave obvious traces on the bioskin
2—Some smudge, make-up leaves some traces on the bioskin
3—Smudge, make-up leaves obvious traces on some part of the bioskin
4—Significant smudge, make-up leaves obvious traces on large area of the bioskin The above Smudging Index is provided in the range from 0 to 4, each number representing a smudge index number wherein a lower number represents low smudging and wherein a larger number represents greater smudging.

Example 5: In-Vitro Smudge Testing of Selected Inventive and Comparative Compositions The above-described in-vitro study was conducted to evaluate the smudge resistance of each of a panel of selected Inventive and Comparative compositions, for which the results are shown in Table 5, below.

TABLE 5

Smudge Testing of Inventive and Comparative Compositions

| Tested Composition | Smudge Index (latex mascara) | Smudge Index (waterproof) |
| --- | --- | --- |
| INV 1 | 1 | 1 |
| INV 2 | 2 | 1 |
| INV 3 | 1 | 2 |
| COMP 1 | 2 | 3 |
| COMP 2 | 2 | 3 |
| COMP 3 | 3 | 2 |
| COMP 4 | 3 | 3 |
| COMP 5 | 3 | 2 |

Figure 6:
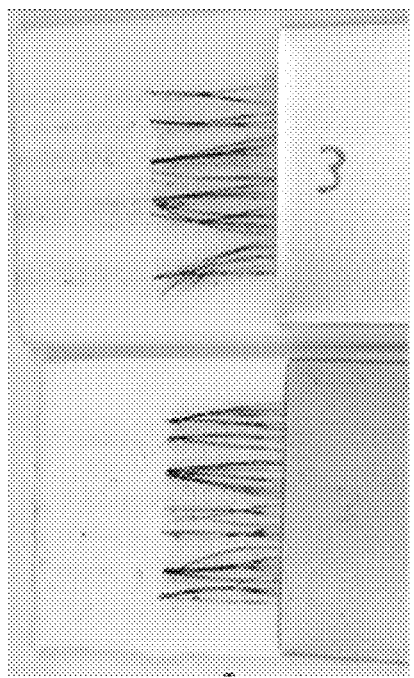
FIG. 6 includes two panels designated as A and B of photographic images demonstrating various degrees of mascara smudging using a high latex mascara.
Figure 6:
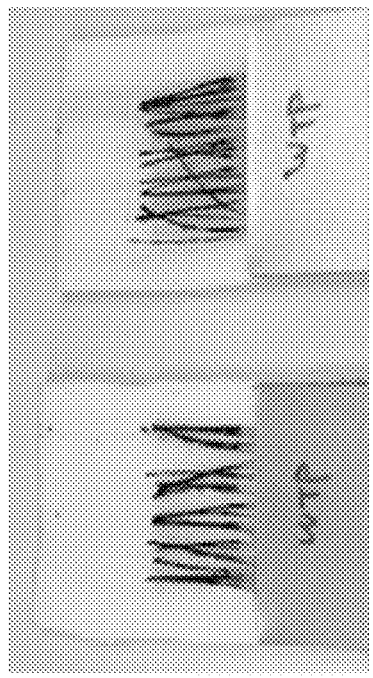

Referring now to the drawings, FIG. 6 shows photographic images of two representative Inventive and Comparative Compositions tested against high latex mascara (FIG. 6A) and waterproof mascara (FIG. 6B), wherein results with INV 1 are shown on the left side of each of FIG. 6A and FIG. 6B, and results with COMP 1 are shown on the right side of each of FIG. 6A and FIG. 6B. As plainly shown, for both types of mascara, INV 1 (which contains rice starch particles) exhibits much less smudging compared with COMP 1 (no starch).

Example 6: Shear Viscosity Evaluation of Selected Inventive and Comparative Compositions In various embodiments, the composition is characterized as having a relatively low viscosity (i.e., less than thickened, cream type O/W, W/O and anhydrous cream cleansers). In some embodiments, as exemplified herein, the viscosity of the inventive composition is less than 1 Pa·s, and that may be in a range from about 0.0016 Pa·s to about 0.0022 Pa·s, or including from about 0.001 Pa·s to less than 1 Pa·s including all increments therebetween.

Shear viscosity was evaluated using a conventional method. In short, a 60 mm 2-degree cone plate is used as a rheology probe with a gap of 60 μm between a bottom plate and the probe. Samples of compositions were prepared as follows: each sample of ~0.5 g of composition was first equilibrated at 25° C. for 20 seconds, then a shear rate flow experiment was performed. The duration of experiment is 10 minutes, shear rate changes from 0.001-200/s, with 5 data points recorded within each decade. After the experiment, a zero-shear viscosity is determined from a log(viscosity) vs. log(shear rate) plot, by linear fitting the plateau region to intersect with y-axis. This value represents the viscosity of each formula under unperturbed situation.

The zero shear viscosity of each tested composition is listed in Table 6 below.

TABLE 6

Zero Shear Viscosity of Selected Inventive and Comparative Compositions

| Tested Composition | Zeroth Shear Viscosity (Pa · s) |
| --- | --- |
| INV 1 | $1.98 \times 10^{-3}$ |
| INV 2 | $2.22 \times 10^{-3}$ |
| INV 3 | $1.76 \times 10^{-3}$ |
| COMP 1 | $1.60 \times 10^{-3}$ |
| COMP 2 | $1.74 \times 10^{-3}$ |
| COMP 3 | $1.65 \times 10^{-3}$ |
| COMP 4 | $2.51 \times 10^{-3}$ |
| COMP 5 | $1.57 \times 10^{-3}$ |

Example 7: Friction Coefficient Evaluation of Selected Inventive and Comparative Compositions In various embodiments, the composition is characterized as having a relatively high coefficient of friction (i.e., greater than some of the comparative compositions, and in particular as compared to cream type O/W, W/O and anhydrous cream cleansers). In some embodiments, as exemplified herein, the coefficient of friction of the inventive composition is greater than 0.30μ and may be in a range from about 0.30μ to about 0.60μ or including from about 0.39μ to about 0.5μ including all increments therebetween. The greater the friction coefficient, the less greasy the composition feels on skin, conferring a fresh fell upon application that does not leave skin feeling oily and thus rendering the composition suitable as a leave-on composition that the consumer need not follow with additional cleansing.

Tribology was used to measure friction coefficient of bioskin after wiped by Selected Inventive and Comparative Compositions. Higher coefficient indicates a less greasy and a squeakier skin finish. In the study, a sample of ~1 g of each tested composition was first deposited onto a piece of cotton round. The treated cotton round was then used to wipe bioskin 5 times. Thereafter, a ring probe was lowered onto the bioskin until the force reached a predetermined amount of force equivalent to about 2N, whereupon the friction coefficient was determined at 2 rad/s.

The friction coefficient of each tested composition is listed in Table 7 below.

TABLE 7

Friction Coefficient of Selected Inventive and Comparative Compositions

| Tested Composition | Friction Coefficient (μ) |
| --- | --- |
| INV 1 | 0.41 |
| INV 2 | 0.5 |
| INV 3 | 0.39 |
| COMP 1 | 0.36 |
| COMP 2 | 0.37 |
| COMP 3 | 0.34 |
| COMP 4 | 0.21 |
| COMP 5 | 0.43 |

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" and "excludes" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples serve to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A cosmetic composition for make-up removal, comprising:
   i. a water-based micellar cleansing system that comprises:
      a. a blend of at least two surfactants, the blend comprising at least one nonionic surfactant having an HLB that is in the range from about 8 to about 16, and at least one surfactant having an HLB that is greater than about 16;
      b. at least one powdered polysaccharide; and
      c. water,
      wherein the blend of the two surfactants form micellar aggregates which are separated out from the water at rest but which temporarily suspend in the water upon agitation of the cosmetic composition.

2. The cosmetic composition according to claim 1, wherein the at least one surfactant having an HLB that is greater than about 16 is essentially free from or excludes cationic surfactants.

3. The cosmetic composition according to claim 1, wherein the at least one surfactant having an HLB that is in the range from about 8 to about 16 is a nonionic surfactant, and the at least one surfactant having an HLB that is greater than about 16 is one of an anionic and an amphoteric surfactant.

4. The cosmetic composition according to claim 1, wherein the at least one surfactant having an HLB that is greater than about 16 is an amphoteric surfactant and has an HLB that is greater than 20.

5. The cosmetic composition according to claim 4, wherein the amphoteric surfactant comprises an alkyl amphoacetates.

6. The cosmetic composition according to claim 1, wherein the at least one powdered polysaccharide is essentially water-insoluble.

7. A cosmetic composition for make-up removal, comprising:
   i. a water-based micellar cleansing system that comprises:
      a. a blend of at least two surfactants, the blend comprising at least one nonionic surfactant having an HLB that is in the range from about 8 to about 16, and at least one surfactant having an HLB that is greater than about 16;
      b. at least one powdered polysaccharide; and
      c. water,
      wherein the at least one powdered polysaccharide comprises particles that are isometric, anisometric or a combination thereof, and each of the particles has each of a length, a width and a thickness dimension that is in the range from about 2 μm to about 150 μm.

8. A cosmetic composition for make-up removal, comprising:
   i. a water-based micellar cleansing system that comprises:
      a. a blend of at least two surfactants, the blend comprising at least one nonionic surfactant having an HLB that is in the range from about 8 to about 16, and at least one surfactant having an HLB that is greater than about 16;
      b. at least one powdered polysaccharide; and
      c. water,
      wherein the at least one powdered polysaccharide comprises particles that are heterogenous in size.

9. The cosmetic composition according to claim 1, wherein the at least one powdered polysaccharide is selected from starches, alginates, celluloses, chitosan, chitin, and combinations thereof.

10. A cosmetic composition for make-up removal, comprising:
   i. a water-based micellar cleansing system that comprises:
      a. a blend of at least two surfactants, the blend comprising at least one nonionic surfactant having an HLB that is in the range from about 8 to about 16, and at least one surfactant having an HLB that is greater than about 16;
      b. at least one powdered polysaccharide; and
      c. water,
      wherein the blend of at least two surfactants includes Peg-7 Glyceryl Cocoate and Disodium Cocoamphodiacetate; and wherein the at least one powdered polysaccharide is selected from *Oryza Sativa* (Rice) Starch, Oxidized Starch Acetate (Tapioca), and combinations thereof.

11. The cosmetic composition according to claim 1, wherein each of the surfactants is present in an amount in the range from about 0.3% to about 5%, based on the total weight of the composition.

12. The cosmetic composition according to claim 1, wherein the at least one powdered polysaccharide is present in an amount in the range from about 0.1% to about 30%, based on the total weight of the composition.

13. The cosmetic composition according to claim 1, wherein water is present in an amount in the range from about 65% to about 99%, based on the total weight of the composition.

14. The cosmetic composition according to claim 1, further including:
   ii. one or more components selected from the group consisting of:
      a. one or more mineral powders;
      b. one or more humectants;
      c. one or more preservatives;
      d. one or more defoaming agents;
      e. one or more cosmetically acceptable additives;
      f. and combinations thereof.

15. The cosmetic composition according to claim 14, wherein one or more of:
   a. the one or more mineral powders, when present, is selected from the group consisting of titanium oxide, Kaolin, silica, fumed silica, talc, mica, and combinations thereof;
   b. the one or more humectants, when present, is selected from Glycerin, Hexylene Glycol, and combinations thereof;
   c. the one or more preservatives, when present, is selected from Myrtrimonium Bromide, Phenoxyethanol, Hydroxyacetophenone and combinations thereof; and
   d. the one or more defoaming agents, when present, comprises Dimethicone (and) Polysorbate 65 (and) Simethicone.

16. The cosmetic composition according to claim 14, wherein one or more of:
   a. each of the one or more mineral powders, when present, is present at a ratio of mineral powder to polysaccharide powder, by weight based on the total weight of the composition, at a ratio in the range from about 1:10 to about 2:1;
   b. each one of the least one humectant, when present, comprises a polyol and is present in an amount in the range from about 0.5% to about 5%, based on the total weight of the composition the at least one humectant; and
   c. each one of the one or more defoaming agent, when present, is present in an amount in the range from about 0.01% to about 1%, based on the total weight of the composition.

17. The cosmetic composition according to claim 14, wherein (i) the one or more cosmetically acceptable additives is selected from fragrances, colorants, essential oils, fruit extracts, citric acid, sodium chloride, neutralizing or pH-adjusting agents, and combinations thereof; and, wherein (ii) the composition is free or essentially free of cationic agents, parabens, formaldehyde, and formaldehyde-derived compounds, antimicrobials that comprise any one or more of caprylyl glycol, phenoxyethanol, hexyl glycerin, ethylhexylglycerin, octylglycerin, benzylglycerin, 3-heptoyl-2,2-propandiol, 1,2-hexandiol, and polyaminopropyl biguanide, and combinations thereof.

18. A cosmetic composition for make-up removal, comprising:
   i. a water-based micellar cleansing system that comprises:
      a. a blend of at least two surfactants, the blend comprising at least one nonionic surfactant having an HLB that is in the range from about 8 to about 16, and at least one amphoteric surfactant; and
      b. at least one powdered polysaccharide comprising essentially water-insoluble particles that are isometric, anisometric or a combination thereof, wherein each of the particles has each of a length, a width and a thickness dimension that is in the range from about 2 μm to about 150 μm, the powdered polysaccharide selected from starches, alginates, celluloses, chitosan, chitin, and combinations thereof; and
   ii. optionally, one or more of additional ingredients selected from inorganic mineral powders, humectants, silicone-based defoaming agents, preservatives, and other cosmetically acceptable additives.

19. The cosmetic composition according to claim 1, wherein the cosmetic composition has a viscosity of less than 1 Pa·s.

20. The cosmetic composition according to claim 19, wherein the cosmetic composition has a viscosity in a range from about 0.0016 Pa·s to about 0.0022 Pa·s.

* * * * *